United States Patent [19]
Vance et al.

[11] 3,988,690
[45] Oct. 26, 1976

[54] AMPLIFIER CIRCUIT HAVING A FLOATING INPUT STAGE

[75] Inventors: Gary Charles Vance, Portland; Richard James Ballard, Beaverton, both of Oreg.

[73] Assignee: Tektronix, Inc., Beaverton, Oreg.

[22] Filed: Oct. 4, 1973

[21] Appl. No.: 403,367

[52] U.S. Cl. ............................ 330/10; 330/165; 330/199
[51] Int. Cl.² .................................... H03F 3/38
[58] Field of Search ............... 330/10, 199, 165; 340/210, 18; 307/264; 332/59, 43 B, 31 R; 328/223, 168

[56] References Cited
UNITED STATES PATENTS

| | | | |
|---|---|---|---|
| 1,890,489 | 12/1932 | Baker | 330/165 X |
| 2,694,114 | 11/1954 | Kalfaial | 330/10 |
| 3,058,066 | 10/1962 | Redding et al. | 330/165 X |
| 3,428,912 | 2/1969 | Wolcott | 330/199 X |
| 3,456,132 | 7/1969 | Dechelotle | 307/296 |
| 3,483,476 | 12/1969 | Kobayashi et al. | 330/10 |
| 3,631,329 | 12/1971 | Kimball | 330/10 X |
| 3,657,717 | 4/1972 | Glantschnig et al. | 340/210 X |

*Primary Examiner*—James B. Mullins
*Attorney, Agent, or Firm*—George T. Noe

[57] ABSTRACT

An input amplifier stage is isolated from the main body of an amplifier and instrument ground by a single transformer which provides both an energy path to the input stage and an amplifier signal path from the input stage using a modulated load technique. The secondary of the transformer, which is connected across the input amplifier, includes a rectifier and filtering components to provide a floating D. C. voltage supply.

5 Claims, 2 Drawing Figures

AMPLIFIER CIRCUIT HAVING A FLOATING INPUT STAGE

BACKGROUND OF THE INVENTION

In many types of instruments such as oscilloscopes and physiological monitoring devices, it is desirable to provide a floating input amplifier which is electrically isolated from the remainder of the instrument. The problem becomes apparent where the object under test is at a different voltage potential than the measurement instrument itself, which is usually at ground potential in accordance with recognized electrical standards. For example, in measuring the ripple on a high-voltage supply to evaluate the efficiency of a regulating circuit, it would be desirable to "float" the input stage at the D.C. level of the supply and thereby avoid a wide difference of potential connected across the input terminals.

A floating input amplifier is particularly important in physiological monitors, where the object under test is a human body. It is essential that any shock hazard be minimized, that is, that power supply potentials within the monitoring device or line voltage from the A.C. mains not reach the patient in the event of an instrument malfunction. Also, it is important from the standpoint of providing an instrument capable of closely monitoring signals being generated from a source which may be totally insulated from ground or any other potential, or which may be subjected to the potentials of other clinical devices connected thereto.

There have been many previous attempts to provide a floating input amplifier for an electronic instrument. One scheme utilized a transformer-isolated amplifier powered by batteries. Not only are batteries bulky and their power limited, but they also require recharging or replacement. Another scheme utilized a pair of transformers; one for an energy path and one for a signal path.

SUMMARY OF THE INVENTION

According to the present invention, a floating input stage is isolated from the main body of an amplifier circuit by means of a single transformer, which both provides power to the input stage and couples a signal therethrough. The primary of the transformer includes a power oscillator connected thereacross and an output amplifier connected to a center tap thereof. The secondary of the transformer includes a full-wave rectifier and filter capacitors connected across the input stage to provide a floating D.C. power supply. The power drawn from the secondary by the input stage is modulated in accordance with an input signal. The modulation is sensed in the primary as a change in required oscillator supply current. The center tap of the transformer primary winding is the summing point for the output amplifier, which produces an output voltage signal which is proportional to the input signal.

It is therefore one object of the present invention to provide an amplifier circuit which has a floating input stage.

It is another object of the present invention to provide an amplifier circuit which has an input stage isolated from instrument chassis ground.

It is a further object of the present invention to provide an amplifier floating input stage which does not require batteries for power.

It is yet another object of the present invention to provide an amplifier circuit in which the input stage is isolated from following stages by a single transformer which provides a single transmission path for both energy to the input stage and signals to the following stages.

Further objects, features, and advantages will be apparent from consideration of the following description taken in conjunction with the accompanying drawings.

DETAILED DESCRIPTION OF THE INVENTION

Figure 1:
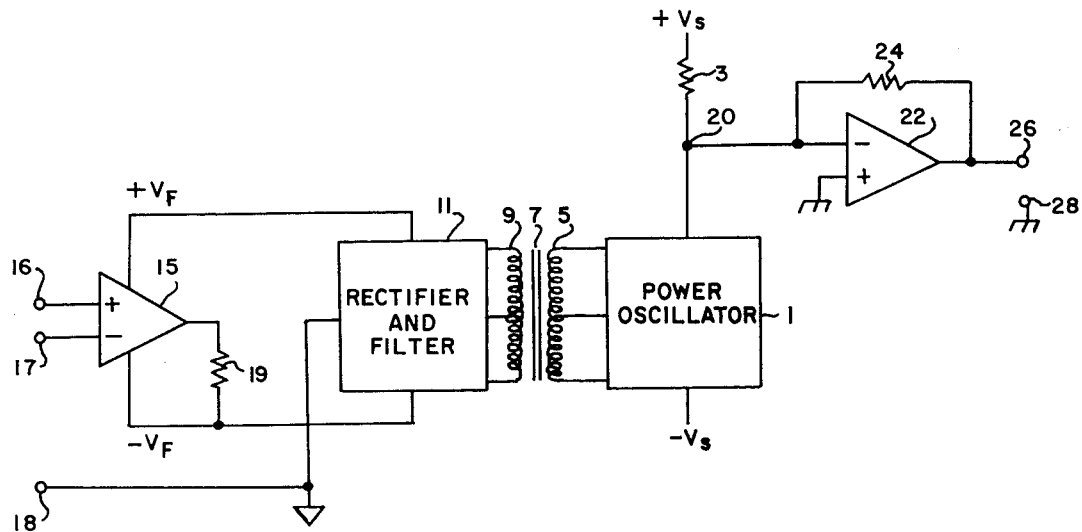
FIG. 1 shows a block diagram of the amplifier circuit and power supply therefor according to the present invention.

Turning now to the block diagram shown in FIG. 1 of the drawings, a power oscillator 1 is shown connected in series with a resistor 3 between a pair of suitable supply voltages, $+V_s$ and $-V_s$. The power oscillator 1, one embodiment of which will be discussed in detail later, generates an A.C. voltage to drive the primary winding 5 of a suitable transformer 7. The A.C. voltage is developed in the proper proportion across the secondary winding 9 and rectified and filtered by a suitable rectifier circuit 11, one embodiment of which will be discussed in detail later, to provide suitable floating supply voltages, $+V_F$ and $-V_F$. The supply voltages $+V_F$ and $-V_F$ are completely isolated from the primary side of transformer 7, and thus have no reference to instrument or chassis ground.

The floating supply voltages $+V_F$ and $-V_F$ are applied across an input amplifier 15, which may be discrete components or a conventional integrated circuit amplifier, to provide power thereto. Amplifier 15 has a pair of floating input terminals 16 and 17 which may be connected to a signal source. Additionally, a terminal 18 is connected to the floating reference potential of the $+V_F$ and $-V_F$ supplies so that a connection may be made to the signal source common, thereby setting the reference level of amplifier 15 at the reference level of the signal source. This operation is known in the art as floating. The input signal applied between terminals 16 and 17 is amplified by amplifier 15, and the amplifier signal is developed across a load resistor 19. The signal variations developed across resistor 19 produce a corresponding signal current which flows from the $+V_F$ supply, through the amplifier 15 output and through resistor 19 to $-V_F$, which signal current correspondingly modulates the power drawn from the secondary winding 9 in proportion to the input signal.

The modulation in the secondary of transformer 7 is reflected into the primary, producing a change in the supply current requirements of the power oscillator 1. Connected between the resistor 3 and power oscillator 1 at junction 20 is the input to an operational amplifier output stage 22, whose other input terminal is connected to chassis ground. Through operational amplifier action, junction 20 is maintained at zero volts, so that the current supply changes required by power oscillator 1 due to application of an input signal between terminals 16 and 17 are delivered via the feedback resistor 24 as the operational amplifier acts to stabilize the voltage at junction 20. The current variations through feedback resistor 24, then, develop a voltage across resistor 24 which is available as an output signal between output terminal 26 and chassis ground 28.

Figure 2:
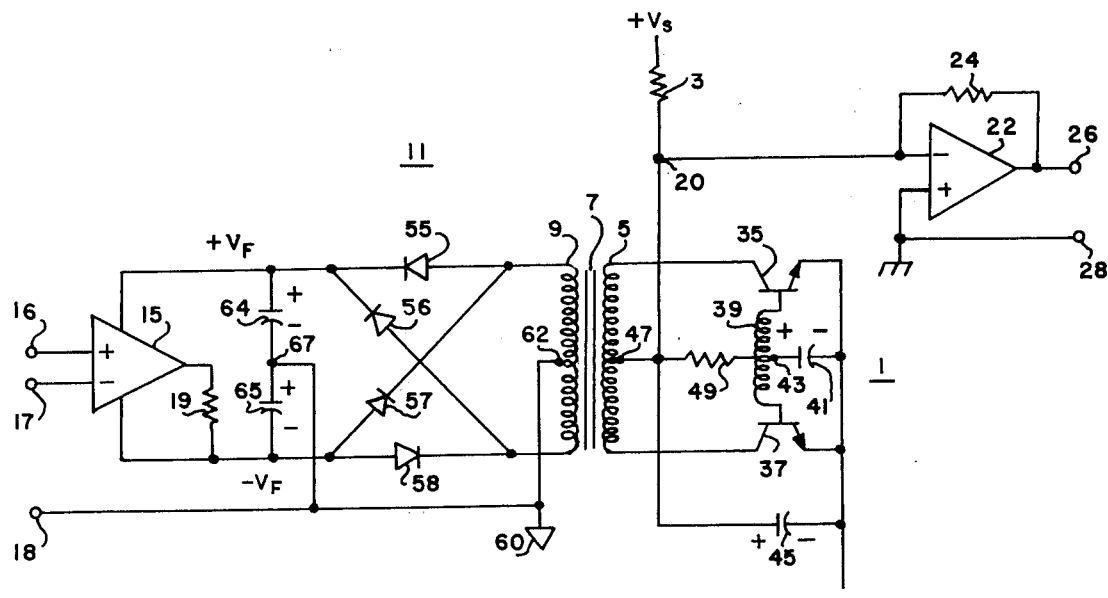
FIG. 2 is a circuit schematic of the amplifier showing details of the signal transmission path and power supply according to the preferred embodiment.

Referring now to FIG. 2, power oscillator 1 is shown comprising a pair of transistors 35 and 37, both having their emitters connected to the $-V_s$ supply voltage. The collector of transistor 35 is connected to one end of primary winding 5, and the collector of transistor 37 is connected to the other end of primary winding 5. The bases of transistors 35 and 37 are connected to opposite ends of a second primary winding 39 of transformer 7. A capacitor 41 is connected between a centertap 43 of primary winding 39 and $-V_s$, and a capacitor 45 is connected between the centertaps 47 and 43. The amplifier null point, or junction 20, is connected to centertap 47.

The rectifier circuit 11 is shown as a conventional bridge-type full-wave rectifier comprising diodes 55, 56, 57, 58, connected across opposite ends of the secondary winding 9 of transformer 7. A floating reference 60 is established at a centertap 62 of secondary winding 9. Filter capacitors 64 and 65 are connected in series across the D.C. voltage output, and the junction 67 between these capacitors is connected to the floating reference so that the floating supply voltages $+V_F$ and $-V_F$ can be established across capacitors 64 and 65.

As can be appreciated from the foregoing discussion, input amplifier 15 can be floated at the level of the signal source to be connected to terminals 16, 17, and 18 since it is isolated from the instrument or chassis ground to which the output amplifier 22 is referred. Further, it can be appreciated that if the input terminals to amplifier 15 are the equivalent of field-effect transistor gates, current cannot be drawn from the $+V_F$ and $-V_F$ supplies in any case by the signal source, minimizing shock hazard or damage due to current surges.

The bandwidth of the amplifier system is primarily determined by the oscillator frequency and the values of capacitors 64, 65, and 45, and the bandwidth of amplifiers 15 and 22.

It will be obvious to those skilled in the art that many changes may be made in the details of the above-described preferred embodiment of the present invention without departing from the spirit of the invention.

We claim:

1. An amplifier system comprising:
    a floating power supply including a transformer having a primary winding and a secondary winding, each of said windings including a center tap, a power oscillator connected across said primary winding and referred to chassis ground, and a full-wave rectifier connected across said secondary winding of said transformer for producing positive and negative D.C. supply voltages with respect to a floating potential at said center tap of said secondary winding;
    a first signal amplifier connected between said positive and negative D.C. supply voltages to receive D.C. power therefrom, said amplifier adapted to receive an input signal and modulate the power drawn from said secondary winding in accordance therewith so that an amplified representation of said signal is reflected into said primary winding; and
    a second signal amplifier having a first input terminal connected to said center tap of said primary winding to sense said reflected signal representation and produce an output signal in accordance therewith so that said output signal is an amplified representation of said input signal.

2. The system according to claim 1 wherein said power oscillator is connected between a first and second source of DC voltage, one of said sources being directly coupled to said center tap on said primary winding to provide a current path through said primary winding to said oscillator, and said second signal amplifier is an operational amplifier having a second input terminal connected to ground to maintain said center tap of said primary winding at virtual ground.

3. An amplifier circuit including a floating input stage, comprising:
    input amplifier means including a load resistor across which an input signal is developed, said input amplifier means electrically isolated from circuit ground;
    D.C. power supply means producing floating D.C. output voltage levels connected to said input amplifier means for providing operating power thereto, said D.C. power supply means including a transformer and a power oscillator connected across a primary winding of said transformer to provide energy for said input amplifier means, said transformer providing a single transmission path to couple said energy thereacross in one direction and said developed signal thereacross in the opposition direction, wherein operating current for said oscillator is varied by said developed signal being reflected from a secondary winding of said transformer to said primary winding; and
    output amplifier means coupled to said power oscillator for responding to said current variation to produce an output signal therefrom, wherein said output signal is a replica of said input signal.

4. The circuit according to claim 3 wherein said D.C. power supply includes a full wave rectifier connected across the secondary winding of said transformer.

5. The circuit according to claim 3 wherein said output amplifier means includes an operational amplifier having its input connected to sense the variation of operating current by said oscillator and provide an output voltage signal proportional thereto.

* * * * *

UNITED STATES PATENT OFFICE
CERTIFICATE OF CORRECTION

PATENT NO. : 3,988,690
DATED : October 26, 1976
INVENTOR(S) : GARY CHARLES VANCE, ET AL It is certified that error appears in the above-identified patent and that said Letters Patent are hereby corrected as shown below:

Column 4, line 41, "opposition" should be --opposite--.

Signed and Sealed this

Eighth Day of March 1977

[SEAL]

Attest:

RUTH C. MASON
Attesting Officer

C. MARSHALL DANN
Commissioner of Patents and Trademarks